United States Patent
Velaga

(10) Patent No.: US 11,847,845 B2
(45) Date of Patent: Dec. 19, 2023

(54) INTEGRATING A WIDGET IN A THIRD-PARTY APPLICATION

(71) Applicant: Orbit Healthcare, Inc., East Brunswick, NJ (US)

(72) Inventor: Krishna Velaga, East Brunswick, NJ (US)

(73) Assignee: ORBIT HEALTHCARE, INC., East Brunswick, NJ (US)

( * ) Notice: Subject to any disclaimer, the term of this patent is extended or adjusted under 35 U.S.C. 154(b) by 0 days.

(21) Appl. No.: 18/097,790

(22) Filed: Jan. 17, 2023

(65) Prior Publication Data

US 2023/0230407 A1    Jul. 20, 2023

Related U.S. Application Data

(63) Continuation-in-part of application No. 17/188,195, filed on Mar. 1, 2021.

(51) Int. Cl.
G06V 30/413 (2022.01)
G06Q 40/08 (2012.01)
G06F 40/279 (2020.01)

(52) U.S. Cl.
CPC .......... G06V 30/413 (2022.01); G06F 40/279 (2020.01); G06Q 40/08 (2013.01)

(58) Field of Classification Search
CPC ..... G06V 30/413; G06F 40/279; G06Q 40/08
See application file for complete search history.

(56) References Cited

U.S. PATENT DOCUMENTS

| 5,832,447 A | 11/1998 | Reiker et al. |
| 8,442,844 B1 * | 5/2013 | Trandal ................ G06Q 30/012 705/35 |
| 2002/0082863 A1 | 6/2002 | Muszynski |

(Continued)

FOREIGN PATENT DOCUMENTS

| JP | 2007048146 A | * | 2/2007 |
| JP | 2007048146 A | | 2/2007 |
| RU | 2607270 C2 | | 1/2017 |

OTHER PUBLICATIONS

Non-Final Office Action (NFOA) issued for U.S. Appl. No. 17/188,195, dated Aug. 10, 2023 (21 pages).

*Primary Examiner* — Pinalben Patel
(74) *Attorney, Agent, or Firm* — Shumaker, Loop & Kendrick, LLP

(57) ABSTRACT

A system and method for integrating a widget in a third-party application. Initially, a widget software code related to insurance payment capture and verification may be received. Further, the widget software code may be integrated into an application code of a third-party application. The widget software code may be executed to invoke an insurance payment widget. The insurance payment widget is configured to capture insurance card images, and extract insurance information based on an analysis of the insurance card images. Furthermore, the extracted insurance information may be validated using an insurance database and plans curated by an application provider. Subsequently, an insurance eligibility status and insurance coverage benefits of the insurance subscriber may be received and used to enable an insurance payment mode on the third party application in real-time, thereby integrating the widget in the third party application.

13 Claims, 4 Drawing Sheets

(56) References Cited

U.S. PATENT DOCUMENTS

| | | | |
|---|---|---|---|
| 2003/0191665 A1 | 10/2003 | Fitzgerald et al. | |
| 2004/0249665 A1* | 12/2004 | David | G06Q 40/08 |
| | | | 705/2 |
| 2005/0192838 A1* | 9/2005 | Jones | G16H 80/00 |
| | | | 705/2 |
| 2006/0047539 A1* | 3/2006 | Huang | G06Q 10/10 |
| | | | 705/2 |
| 2013/0204645 A1* | 8/2013 | Lehman | G06Q 40/08 |
| | | | 705/4 |
| 2021/0124919 A1 | 4/2021 | Balakrishnan et al. | |
| 2021/0209694 A1* | 7/2021 | Tabbaa | G16H 15/00 |
| 2022/0148053 A1 | 5/2022 | Lockhart et al. | |
| 2022/0159129 A1 | 5/2022 | Abe et al. | |
| 2022/0164573 A1 | 5/2022 | Chikyu et al. | |

* cited by examiner

INTEGRATING A WIDGET IN A THIRD-PARTY APPLICATION

PRIORITY INFORMATION

The present application is a continuation-in-part claiming priority from U.S. patent application Ser. No. 17/188,195 filed on Mar. 1, 2021.

TECHNICAL FELD

The present subject matter described herein, in general, relates to a system and a method for integrating a widget in a third-party application.

BACKGROUND

With the world increasingly operating in a digital economy, businesses are striving to adapt the three main constituents of digital economy namely, infrastructure, c-business, and e-commerce. While most businesses have a well-developed infrastructure, they lack the computer-based operational, which is e-business and e-commerce. Even the organizations that carry out their business activities through the internet (e-business), struggle with the e-commerce since the integration with the many payment service providers for the e-commerce could be a daunting task.

Insurance payment gateway is a middleware that allows an e-business to integrate with insurance platforms to facilitate transactions. However, a business has to have the right resources to carry out the complex integrations. If the business does not have programming muscles to flex, let alone the time to build something then it becomes a challenge in itself. For example, a developer may have to write the entire software code and resolve multiple bugs while execution of the software code. It takes lot of time and effort to write, resolve the bugs, and correctly integrate the insurance payment method into the application.

Further, when transactions are performed over decentralized, distributed environments then the time, money, and skills needed to authenticate the transactions increases. Thus, there is a need for simpler mechanisms to help smooth the process of integrating insurance widget in a third-party application, authenticating insurance information and for receiving funds online.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for integrating a widget in a third party application. This summary is not intended to identify essential features of the claimed subject matter nor is it intended for use in determining or limiting the scope of the claimed subject matter.

In one implementation, a method for integrating a widget in a third party application is disclosed. Initially, a widget software code related to insurance payment capture and verification may be received. In one aspect, the widget software code may be received in the form of a script or a web URL and does not require any reconfiguration or user intervention as in a plug and play software. Further, the widget software code may be integrated into an application code of a third-party application. Furthermore, the widget software code may be executed to invoke an insurance payment widget. In one aspect, the insurance payment widget may be configured to capture insurance card images. Subsequently, insurance information may be extracted by an analysis of the insurance card images. The insurance information may be associated with an insurance provider, insurance subscriber/Member ID (MID), and Group Number. The extracted insurance information may be further validated using a proprietary database of the insurance provider and insurance plans curated by an application provider. Further, an insurance eligibility status and insurance coverage benefits of the insurance subscriber may be automatically requested from the insurance provider. Furthermore, the insurance eligibility status and the insurance coverage benefits of the insurance subscriber may be received from the insurance provider in real-time. Finally, an insurance payment mode may be enabled on the third-party application based on the received insurance eligibility status and the insurance coverage benefits in real-time, thereby integrating the widget in the third-party application. In one aspect, the aforementioned method for integrating a widget in a third-party application may be performed by a processor using programmed instructions stored in a memory.

In another implementation, a non-transitory computer program product having embodied thereon a computer program for integrating a widget in a third-party application is disclosed. The program may comprise a program code for receiving a widget software code related to insurance payment capture and verification. In one aspect, the widget software code may be received in the form of a script or a web URL and does not require any reconfiguration or user intervention as in a plug and play software. Further, the program may comprise the program code for integrating the widget software code into an application code of a third-party application. Furthermore, the program may comprise the program code for executing the widget software code to invoke an insurance payment widget. In one aspect, the insurance payment widget may be configured to capture insurance card images. Subsequently, insurance information may be extracted by an analysis of the insurance card images. The insurance information may be associated with an insurance provider, an insurance subscriber/Member ID (MID), and Group Number. Further, the extracted insurance information may be validated using a proprietary database of the insurance provider and insurance plans curated by an application provider. Further, an insurance eligibility status and insurance coverage benefits of the insurance subscriber may be automatically requested from the insurance provider. Furthermore, the insurance eligibility status and the insurance coverage benefits of the insurance subscriber may be received from the insurance provider in real-time. Finally, an insurance payment mode may be enabled on the third-party application based on the received insurance eligibility status and the insurance coverage benefits in real-time, thereby integrating the widget in the third party.

BRIEF DESCRIPTION OF THE DRAWINGS

The foregoing detailed description of embodiments is better understood when read in conjunction with the appended drawings. For the purpose of illustrating the present subject matter, an example is provided as figures, however, the invention is not limited to the specific method and system for integrating a widget in a third party application is disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

Figure 1:
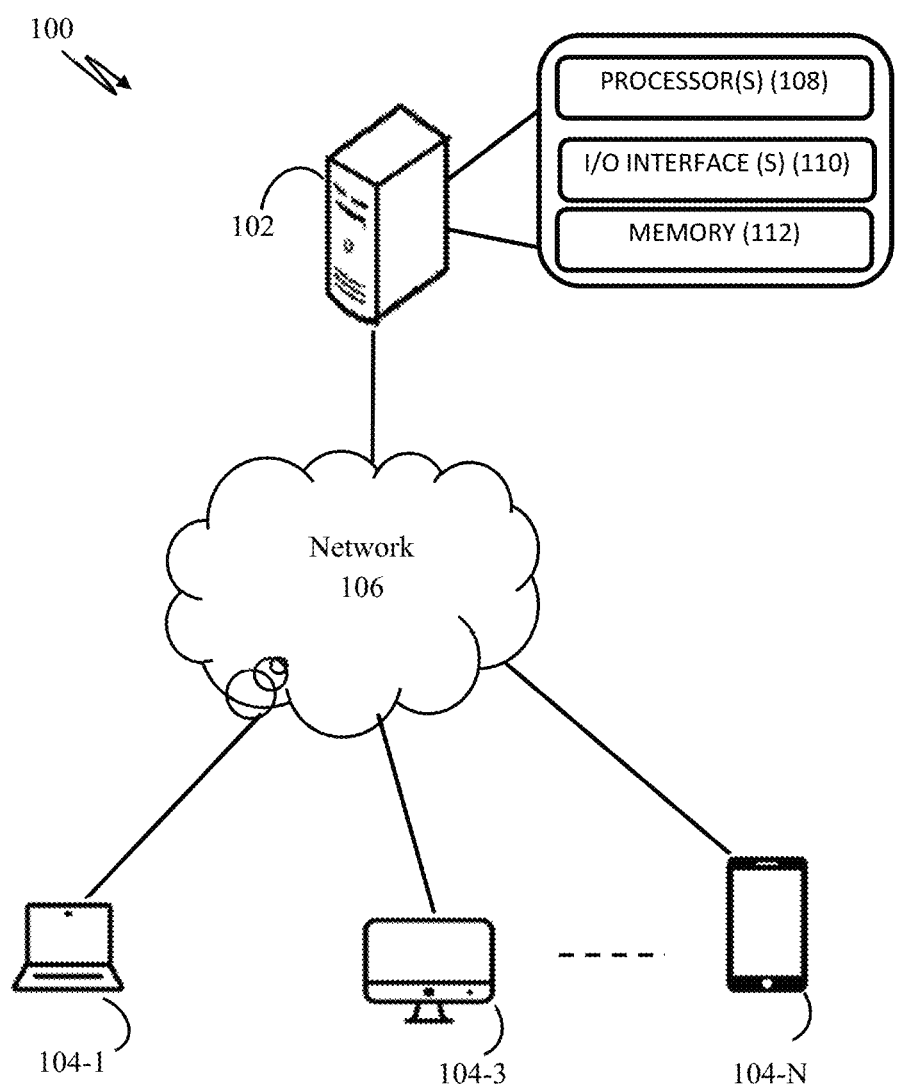
FIG. 1 illustrates a network implementation of a system for integrating a widget in a third-party application is disclosed, in accordance with an embodiment of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving", "integrating," "executing," "enabling," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for integrating a widget in a third-party application. Typically, a developer needs to write an entire software code in order to enable new payment method in an application. However, it takes lot of time and efforts to write the code and implement the code on the application. The present invention discloses the integration of a widget in a third-party application. Initially, a widget software code related to insurance payment capture and verification may be received in the form of a script or a URL. Further, the widget software code may be integrated in an application code of the third-party application by accessing the widget software code and executing the widget software code. Furthermore, executing the widget software code invokes an insurance payment widget. The insurance payment widget may be further configured to enable an insurance payment mode on the third-party application.

In one embodiment, the present invention may enable an insurance payment mode on a third-party application in real-time. Further, the present invention may integrate a widget software code into an application code of the third-party application using a no code low code technique. In one aspect, the no code low-code technique may enable reuse of the widget software code such that the user can drag and drop the widget software code into the application code of the third-party application. The no code low code technique may be configured to reduce complexity of integrating an insurance payment mode into the third-party application. Furthermore, the present invention may be configured to retrieve insurance eligibility status and the insurance coverage benefits of the insurance subscriber from the insurance provider in real-time. Furthermore, the present invention may be configured to reduce the time of integrating the widget software code into the application code.

While aspects of described system and method for integrating a widget in a third-party application may be implemented in any number of different computing systems, environments, and/or configurations, the embodiments are described in the context of the following exemplary system.

Referring now to FIG. 1, a network implementation 100 of a system 102 for integrating a widget in a third-party application is disclosed. It may be noted that one or more users may access the system 102 through one or more user devices 104-1, 104-2 . . . 104-N, collectively referred to as user devices 104, hereinafter, or applications residing on the user devices 104. In one aspect, the one or more users may be a patient, a patient's attender and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are coupled to the system 102 for communications purposes through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Secured Hypertext Transfer Protocol (HTTPS), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. Processors 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a command line interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for integrating a widget in a third party application. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for integrating a widget in a third-party application. The third-party application may be one of a web application, a mobile application and a desktop application. The system 102 may receive a widget software code related to insurance payment capture from card images and verification. In one embodiment, the insurance payment capture and verification may correspond to the verification related to enablement of the insurance payment mode. In another embodiment, the insurance payment capture and verification may be configured to capture payment information from the user, verified the payment information and enable the insurance payment mode. In an aspect, the widget software code may be received at the third-party application. The widget software code may be one of a script or a web Uniform Resource Locator (URL). The widget software code may be plug and play. In one aspect, the widget software code may be easy to use. In the aspect, the widget software code may be added into any third-party application code and executed to enable the insurance payment mode in the third-party application. In one aspect, the widget software code may be a Low-code software having two to three lines of code. In another aspect, the widget software code may be a No-code software which is highly configurable and all plug-and-play.

Once the widget software code is received, the system 102 may integrate the widget software code into an application code of the third-party application. In one example, the widget software code may be the URL. Further, the URL may be received at the third-party application. Furthermore, the received URL may be added into the application code.

Upon integration, the system 102 may execute the widget software code. In one aspect, the execution of the widget software code comprises invoking a pre-programmed application stored in a remote server. The pre-programmed application may be related to an insurance payment widget. Therefore, the execution of the widget software code invokes the insurance payment widget in real-time on the third-party application. In one aspect, the invocation of the insurance payment widget may correspond to opening a window of the insurance payment widget on the third-party application.

Further, the insurance payment widget may be configured to capture insurance card images. The insurance card images may be received from a user. The user may be one of a patient, a patient's guarantor or guardian, an accountant and the like. In one aspect, the insurance card images may represent a front side image and a back side image of an insurance card. In one example, the insurance card may be a health insurance card of the user.

Upon receiving the images, the insurance payment widget may be configured to analyze the insurance card images. In one embodiment, the analysis may comprise preprocessing of the insurance card images using an Artificial Intelligence (AI) technique. In an aspect, the preprocessing may comprise cropping the insurance card images, reducing noise from the insurance card images, and detecting lines, text or images on the insurance card images. In an aspect, a trained data model may be used for the preprocessing of the insurance card images. The trained data model may comprise trained data. The trained data may comprise historical insurance card images, historical cropped images, historical detection information and the like related to multiple subscribers. In one embodiment, the AI technique may use the trained data model for the preprocessing of the insurance card images to identify information of the insurance provider from the images.

Further, the insurance card images may be analyzed using an Optical Character Recognition (OCR) technique. The OCR technique may use one or more text recognition algorithms, such as a matrix matching algorithm or a feature extraction algorithm.

Based on an analysis of the insurance card images, the system 102 may extract insurance information from the insurance card images. The insurance information may be extracted by an analysis of the insurance card images. The insurance information may be associated with an insurance provider, an insurance subscriber/Member ID (MID), Group Number, and other relevant data elements. In one aspect, the insurance provider may be an insurance agency that provides insurance coverage to the user such as a health insurance provider. The information related to the insurance provider may comprise an insurance agency name, an insurance agent name and the like. Further, the insurance subscriber may be the user. The information related to the insurance subscriber may be a subscriber name, a subscriber photo, a subscriber's address and the like. Furthermore, the MID may be a unique number associated to the insurance subscriber. In one example, the MID may be a combination of numbers and characters. In the example, the MID may be AP1098. The MID may be allocated by the insurance provider.

Subsequently, the system 102 may validate the extracted insurance information. The insurance information may be validated using a proprietary database of the insurance provider and insurance plans curated by an application provider. In an aspect, the system 102 may be configured to map an insurance plan type from the insurance plan received from the insurance provider to the third-party application. The proprietary database may be referred to as an insurance provider database. The proprietary database may comprise data corresponding to the MID, the subscriber's name, the subscriber photo, the subscriber's address, a subscriber's coverage and the like. In one aspect, the system 102 may crosscheck the MID of the insurance subscriber with the MID in the proprietary database in real time. If the MID matches, the system 102 may check the subscriber's name. In one aspect, the system 102 may compare the MID and the subscriber's name with the data in the insurance database. Based on the comparison, the system 102 may validate the information of the insurance subscriber. In one embodiment, if the MID matches, then the subscriber is the valid subscriber of the insurance provider. In another embodiment, if the MID does not matches, then the subscriber is an invalid subscriber i.e., not the subscriber of the insurance provider. In an aspect, the system 102 may check if the information related to the insurance subscriber is correctly available in the proprietary database of the insurance provider or not. In another aspect, the system 102 may check if the insurance subscriber is a valid user or not.

Further, the system 102 may automatically request to the insurance provider for an insurance eligibility status and insurance coverage benefits of the insurance subscriber. In one aspect, the system 102 may request to an insurance provider platform. The insurance eligibility status may indicate an active status or an inactive status of the subscriber's insurance. Further, the insurance coverage benefits may indicate a coverage status and benefits of the insurance to the insurance subscriber.

In response to the request, the system 102 may receive the insurance eligibility status and the insurance coverage benefits of the insurance subscriber from the insurance provider platform in real-time. The insurance eligibility status and the insurance coverage benefits of the insurance subscriber may be received in real-time.

Further, if the MID matches, and the coverage is in active status, the system may verify the eligibility of the subscriber. In an embodiment, the eligibility of the subscriber can be verified by comparing the outstanding charge value against the sum insured through the insurance plan. Further, the insurance payment widget may verify whether the insurance plan is active or expired as of the date of service. Based on the comparison, the insurance payment widget may confirm the validation of the insurance coverage benefits to the third-party application.

Upon validation, the system 102 may enable the insurance payment mode on the third party application. The insurance payment mode may be enabled based on the received insurance eligibility status and the insurance coverage benefits. In one aspect, the insurance payment mode may be enabled instantaneously at the time of integration of the widget software code into the application code. Enabling the insurance payment mode, renders user selectable controls on a User Interface (UI) of the third-party application. The user selectable controls may be in the form of radio buttons, drop down list, fields, checkboxes, choice chips or toggle switches for receiving inputs corresponding to an insurance payment. In one aspect, the user may use the insurance payment mode as mode of payment in the third-party application in real-time.

In one embodiment, a payable amount may be displayed to the user on the third-party application. Further, the user may use the insurance pay button to pay the payable amount using an insurance card. In one aspect, the system may receive the insurance card images from the user. Further, the information associated with the user may be validated by analyzing the insurance card images and the insurance database. Based on the validation, the system 102 may further check the insurance eligibility status and the insurance coverage benefits of the user. Further, the system 102 may allow the user to use insurance as method of payment using the insurance pay button, when the insurance payment status and the insurance coverage benefits matches a criteria. The criteria may include the date of service being less than or equal to a date of validity of the insurance eligibility. Further, the payable amount being less than or equal to the insurance coverage benefits.

Figure 2:
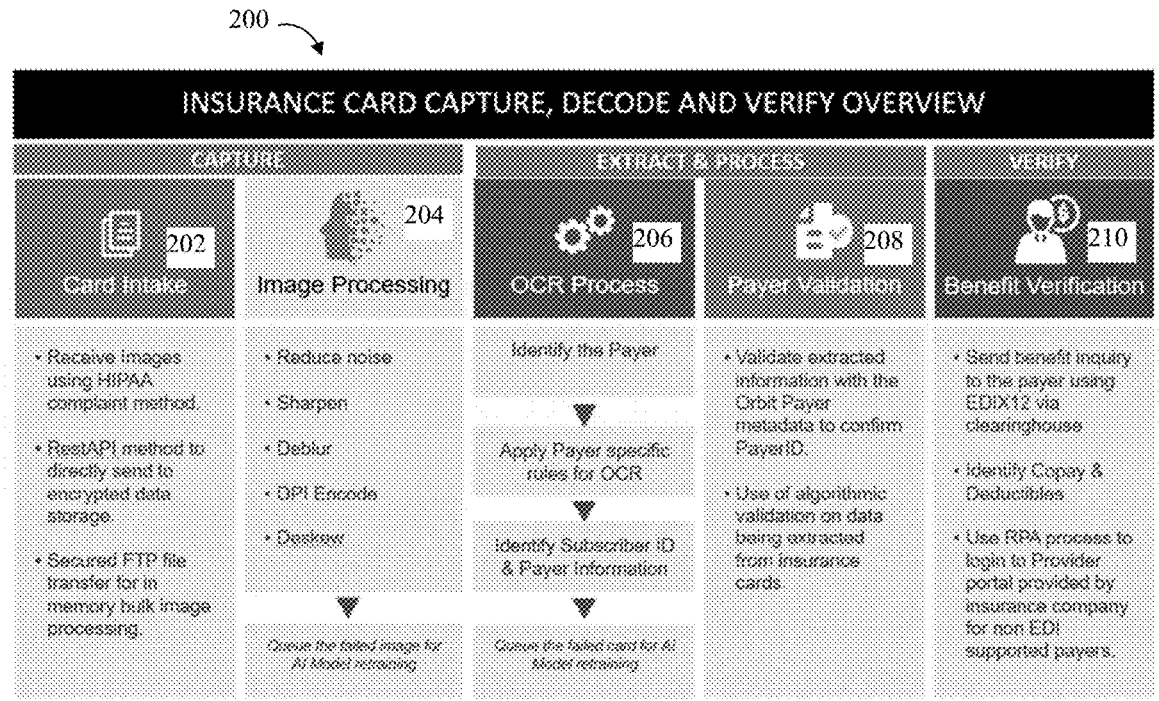
FIG. 2 illustrates an insurance card OCR and eligibility, in accordance with an embodiment of the present subject matter.

Referring now to FIG. 2, an insurance card OCR and eligibility verification 200 is shown, in accordance with an embodiment of the present subject matter. In an embodiment, at a card intake module 202, the system 102 may be configured to receive insurance card images. In the embodiment, the insurance card images may be received using Health Insurance Portability and Accountability Act (HIPAA) complaint method. In an aspect, the HIPAA Compliant method may be a process by which covered entities need to protect and secure a patient's healthcare data or Protected Health Information. The system 102 may use RestAPI method to directly send the insurance card images to an encrypted data storage. Further, the system 102 may transfer secured FTP file to an image processing module 204.

Further, at the image processing module 204, the system 102 may be configured to analyze the insurance card images using an Artificial Intelligence (AI) technique. The analysis of the insurance card images may comprise reducing noise, sharpening the images, deblurring the images, DPI encoding of the images. DE skewing, classifying, and extracting desired card objects. The system 102 may extract text or images from the insurance card images by analysis of the insurance card images. In one aspect, the system 102 may queue the failed images for retraining data stored in a trained data model used by the AI technique.

Subsequently, the system 102 may perform Optical Character Recognition (OCR) technique on the insurance card images at an OCR process module 206. Upon performing the OCR technique, the system 102 may identify a payer as mentioned on the insurance card images. The payer may be an insurance provider. In an aspect, the system 102 may apply the payer specific rules for the OCR. The OCR technique may help to identify a subscriber ID and payer information. In one embodiment, the system 102 may store the failed OCR for retraining the trained data model.

Further, the system 102 may validate the payer information at payer validation module 208. In an aspect, the system 102 may validate the OCR extracted information with payer metadata in order to verify a payerID. The system 102 may use algorithmic validation on the OCR extracted information from the insurance card images.

The system 102 may further verify insurance coverage benefits and an insurance eligibility status of the subscriber at a benefit verification module 210. In an embodiment, the system 102 may send a benefit inquiry to the payer using EDI. In one aspect, the EDI may be a unique ID assigned to each insurance company. It allows provider and payer systems to talk to one another to verify eligibility, benefits and submit claims.

The benefit inquiry may comprise information related to the insurance coverage benefits and the insurance eligibility status associated with the subscriber. The system 102 may use Robotic process automation (RPA) to login to an insurance provide portal for non-EDI payers. The non-EDI payers may be a non-subscriber of the insurance provider. The system 102 may enable an insurance payment mode based on the verification of the insurance eligibility status and the insurance coverage benefits of the insurance subscriber.

Figure 3:
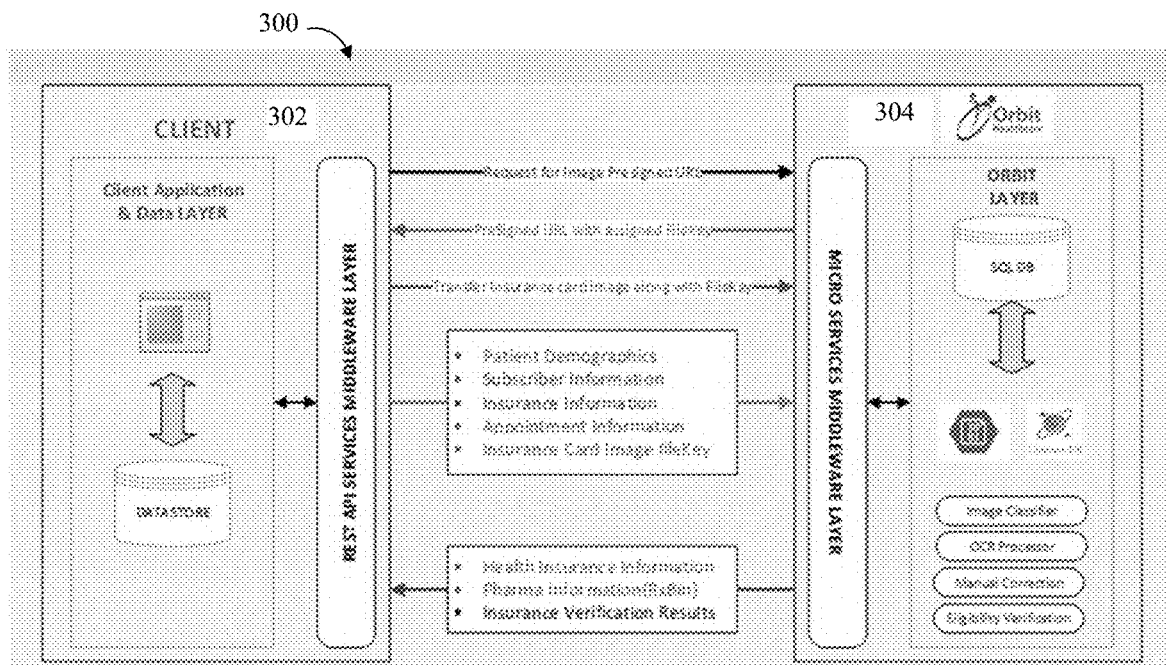
FIG. 3 illustrates an integration of a widget in a third party application, in accordance with an embodiment of the present subject matter.

Referring now to FIG. 3, an integration of a widget in a third party application 300 is illustrated, in accordance with an embodiment of the present subject matter. In an embodiment, a client 302 may be a third party application. Further, a system 102 may be located at the client 302. The system 102 may request SAS token i.e., URL for image upload. Further, an insurance payment widget 304 may open the URL for the image upload. The insurance payment widget 304 may respond to the SAS token. The system 102 may further upload insurance card images using the SAS token. In an aspect, the system 102 may transfer patient demographics, subscriber information, insurance information, and appointment information to the insurance payment widget 304.

Upon receiving the insurance card images, the insurance payment widget 304 may analyze the insurance card images. The insurance payment widget 304 may use image classifier and OCR processor to analyze the insurance card images. The image classifier may be performed for noise reduction, and detect lines or text from the insurance card images. Further, the OCR processor may be configured to detect text from the insurance card images. Upon detection of the text, an insurance eligibility status and insurance eligibility coverage may be verified using a proprietary database of an insurance provider. Upon verification, the insurance payment widget may provide health insurance information, pharma information and insurance verification results to the system 102. Further, the system 102 may enable an insurance payment mode as a mode of payment at the third-party application for the patient in real-time.

Figure 4:
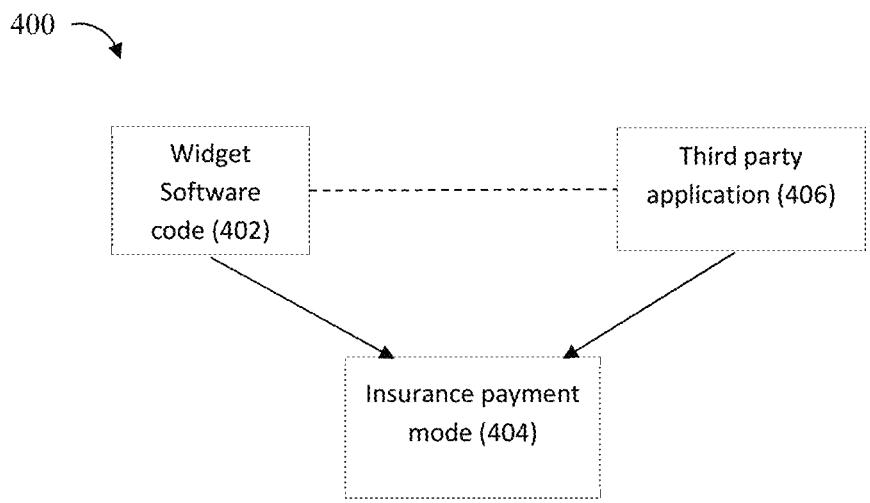
FIG. 4 illustrates an enablement of an insurance payment mode, in accordance with an embodiment of the present subject matter.

Referring now to FIG. 4, an enablement of an insurance payment mode 400, in accordance with an embodiment of the present subject matter is illustrated. In an embodiment, a widget software code 402 may be received. The widget software code 402 may be related to an insurance payment mode 404. In one exemplary embodiment, an owner of a third-party application 406 may want to enable the insurance payment mode 404 at the third-party application 406.

In the exemplary embodiment, the third-party application 406 may receive the widget software code 402. Further, the widget software code 402 may be integrated into an application code of the third-party application 406. The widget software code 402 may be executed to invoke an insurance payment widget at the third-party application 406. The insurance payment widget may be configured to capture insurance card images from the user. Further, the insurance card images may be analyzed to extract information related to an insurance provider, an insurance subscriber/Member ID (MID). Further, the insurance payment widget may validate the extracted information using a proprietary database associated with the insurance provider. Upon validation, a request for an insurance eligibility status and insurance coverage benefits of the insurance subscriber may be automatically transmitted to an insurance platform. Further, an insurance payment mode may be enabled based on receiving the insurance eligibility status and the insurance coverage benefits of the insurance subscriber.

In one embodiment, the widget software code 402 may be integrated into the third-party application 406 using no code low code technique. Upon integration, the insurance payment widget may be invoked in the third-party application 406. Based on the invoking of the insurance payment widget, the insurance payment mode may be enabled on the third-party application.

Figure 5:
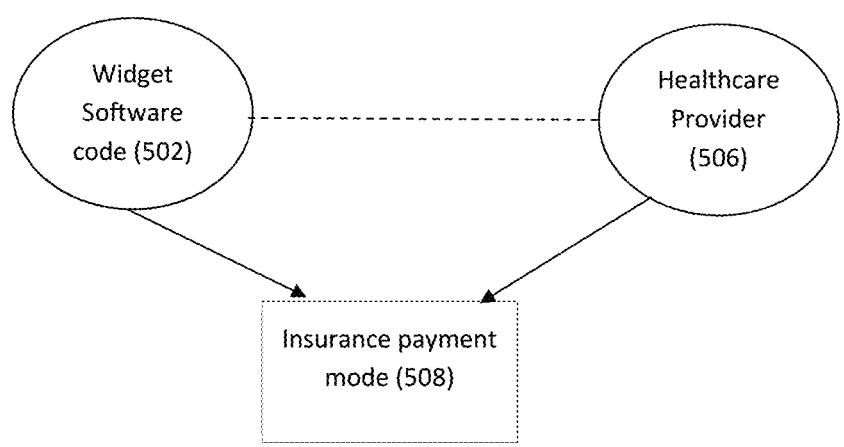
FIG. 5 illustrates an exemplary embodiment of an integration of the widget in the third-party application, in accordance with an embodiment of the present subject matter.

Referring now to FIG. 5, an exemplary embodiment of an integration of a widget in a third-party application 500 is illustrated, in accordance with an embodiment of the present subject matter. In the exemplary embodiment, the third-party application may be an application used by a healthcare provider 506. In one aspect, the healthcare provider 506 may want to integrate an insurance payment widget. In the aspect, the application of the healthcare provider 506 may receive the widget software code 502 related to the insurance payment widget. Further, the widget software code 502 may be integrated into an application code of the healthcare provider 506. The widget software code 502 may be further executed to invoke the insurance payment widget on the application of the healthcare provider 506.

The insurance payment widget may be configured to capture insurance card images. Further, insurance information associated with an insurance provider, an insurance subscriber/Member ID (MID) may be extracted based on an analysis of the insurance card images. The extracted insurance information may be validated using a proprietary database and plans curated by an application provider. Further, a request is sent to the insurance provider, to provide an insurance eligibility status and insurance coverage benefits of the insurance subscriber. Once the insurance eligibility status and the insurance coverage benefits are received, an insurance payment mode may be enabled on the application of the healthcare provider 506.

Figure 6:
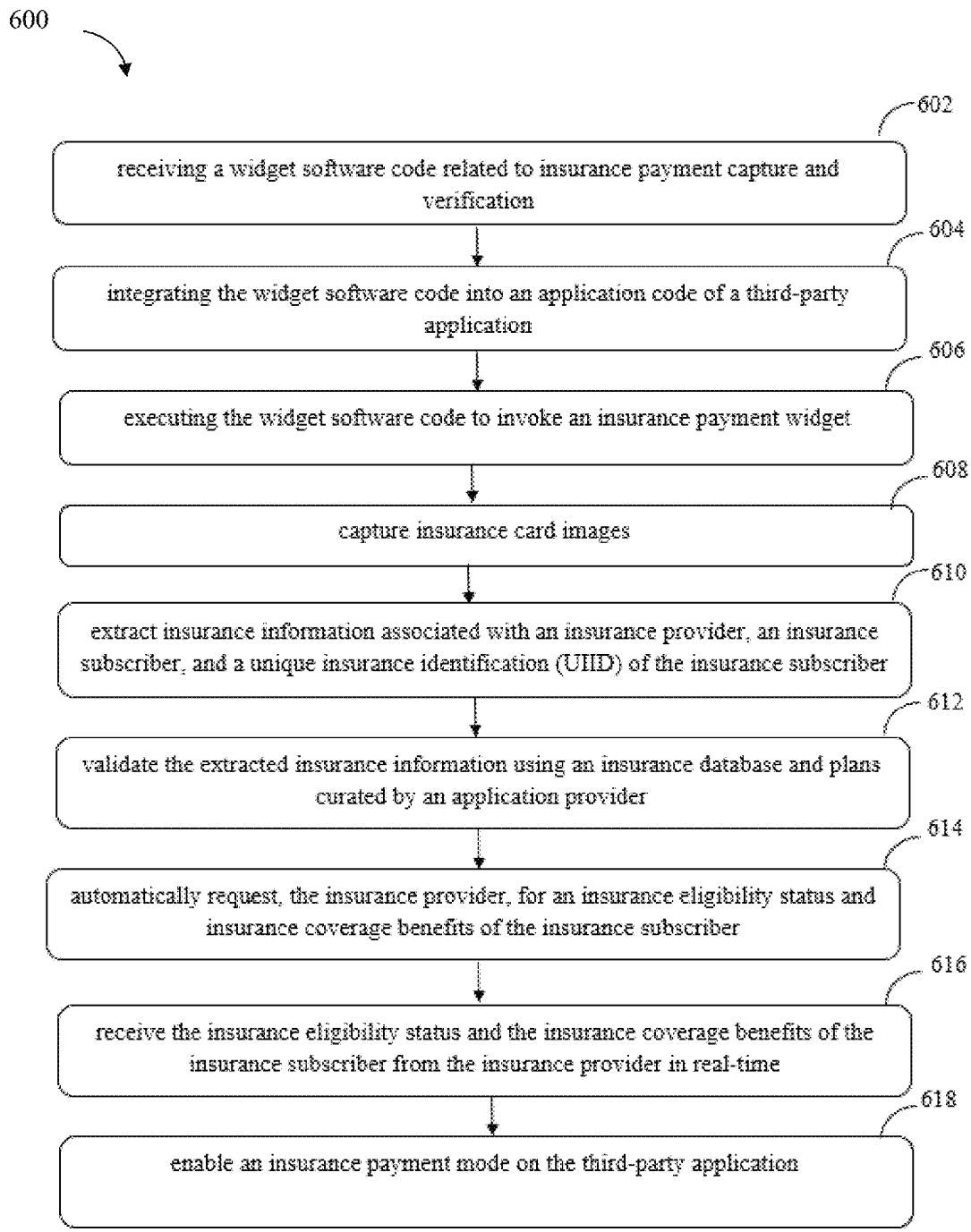
FIG. 6 illustrates a method for integrating a widget in a third-party application, in accordance with an embodiment of the present subject matter.

Referring now to FIG. 6, a method 600 for integrating a widget in a third-party application is shown, in accordance with an embodiment of the present subject matter. The method 600 may be described in the general context of computer executable instructions. Generally, computer executable instructions can include routines, programs, objects, components, data structures, procedures, modules, functions, etc., that perform particular functions or implement particular abstract data types.

The order in which the method 600 is described is not intended to be construed as a limitation, and any number of the described method blocks can be combined in any order to implement the method 600 or alternate methods for integrating a widget in a third-party application. Additionally, individual blocks may be deleted from the method 600 without departing from the spirit and scope of the subject matter described herein. Furthermore, the method 600 for integrating a widget in a third-party application can be implemented in any suitable hardware, software, firmware, or combination thereof. However, for ease of explanation, in the embodiments described below, the method 600 may be considered to be implemented in the above-described system 102.

At block 602, a widget software code related to insurance payment capture and verification may be received at a third-party application. In one aspect, the widget software code may be one of a script or a web URL. The widget software code may be plug and play.

At block 604, the widget software code may be integrated into an application code of the third-party application.

At block 606, the widget software code may be executed to invoke an insurance payment widget. In one aspect, the insurance payment widget is configured to capture insurance card images at block 608.

At block 610, insurance information may be extracted by an analysis of the insurance card images. The insurance information may be associated with an insurance provider, an insurance subscriber/Member 1D (MID), and Group number.

At block 612, the extracted insurance information may be validated using a proprietary database and insurance plans curated by an application provider.

At block 614, an insurance eligibility status and insurance coverage benefits of the insurance subscriber may be automatically requested to the insurance provider.

At block 616, the insurance eligibility status and the insurance coverage benefits of the insurance subscriber may be received from the insurance provider in real-time.

At block 618, an insurance payment mode may be enabled on the third-party application based on the received insurance eligibility status and the insurance coverage benefits in real-time, thereby integrating the widget in the third-party application.

Exemplary embodiments discussed above may provide certain advantages. Though not required to practice aspects of the disclosure, these advantages may include those provided by the following features.

Some embodiments of the system and the method integrates an insurance payment widget into a third party application using no code low code technique.

Some embodiments of the system and the method enable an insurance payment mode on a third party application based on an integration of the insurance payment widget in the third party application.

Some embodiments of the system and the method enable receiving insurance eligibility status and insurance coverage benefits in real time.

Although implementations for methods and system for integrating a widget in a third-party application have been described in language specific to structural features and/or methods, it is to be understood that the appended claims are not necessarily limited to the specific features or methods described. Rather, the specific features and methods are disclosed as examples of implementations for integrating the widget in the third-party application.

The invention claimed is:

1. A method to integrate a widget in a third-party application, the method comprising:
at the third-party application:
receiving, by a processor, a widget software code related to insurance payment capture and verification, wherein the widget software code is one of a script or a web URL, and wherein the widget software code is plug and play;
integrating, by the processor, the widget software code into an application code of the third-party application; and
executing, by the processor, the widget software code to invoke an insurance payment widget, wherein the insurance payment widget is configured to:
capture one or more insurance card images, wherein the one or more insurance card images are received from a user;
extract insurance information based on the analysis of the insurance card images, wherein the insurance information is associated with an insurance provider, an insurance subscriber/Member ID (MID), and a Group Number;
validate the extracted insurance information using a proprietary database of the insurance provider and insurance plans curated by an application provider;
automatically request, the insurance provider, for an insurance eligibility status and insurance coverage benefits of the insurance subscriber;
receive the insurance eligibility status and the insurance coverage benefits of the insurance subscriber from the insurance provider in real-time; and
enable an insurance payment mode on the third-party application based on the received insurance eligibility status and the insurance coverage benefits in real-time, thereby integrating the widget in the third-party application.

2. The method as claimed in claim 1, wherein the method further comprises translating the insurance plan received from the insurance provider to the third-party application.

3. The method as claimed in claim 1, wherein the execution of the widget software code comprises invoking a pre-programmed application stored in a remote server.

4. The method as claimed in claim 1, wherein the insurance payment mode is enabled in the third-party application using the insurance payment widget with no code low code technique.

5. The method as claimed in claim 1, wherein the third-party application is one of a web application, a mobile application,. and a desktop application.

6. The method as claimed in claim 1, wherein the insurance information is captured using Artificial Intelligence (AI) based image processing and Optical Character Recognition (OCR) technique on insurance cards.

7. A system to integrate a widget in a third-party application, the system comprising:
a memory; and
a processor coupled to the memory, wherein the processor is configured to execute instructions stored in the memory to:
at the third-party application:
receive a widget software code related to insurance payment capture and verification, wherein the widget software code is one of a script or a web URL, and wherein the widget software code is plug and play;
integrate the widget software code into an application code of the third-party application; and
execute the widget software code to invoke an insurance payment widget, wherein the insurance payment widget is configured to:
capture one or more insurance card images, wherein the one or more insurance card images are received from a user;
extract insurance information by an analysis of the insurance card images, wherein the insurance information is associated with an insurance provider, an insurance subscriber/Member ID (MID), and Group Number;

validate the extracted insurance information using a proprietary database of the insurance provider and insurance plans curated by an application provider;

automatically request, the insurance provider, for an insurance eligibility status and insurance coverage benefits of the insurance subscriber;

receive the insurance eligibility status and the insurance coverage benefits of the insurance subscriber from the insurance provider in real-time; and enable an insurance payment mode on the third-party application based on the received insurance eligibility status and the insurance coverage benefits in real-time, thereby integrating the widget in the third-party application.

8. The system as claimed in claim 7, wherein the processor is further configured to translate the plan information received from the insurance provider to the third-party application.

9. The system as claimed in claim 7, wherein the execution of the widget software code comprises invoking a pre-programmed application stored in a remote server.

10. The system as claimed in claim 7, wherein the insurance payment mode is enabled in the third-party application using the insurance payment widget with no code low code technique.

11. The system as claimed in claim 7, wherein the third-party application is one of a web application, a mobile application, and a desktop application.

12. The system as claimed in claim 7, wherein the insurance information is captured using Artificial Intelligence (AI) based image processing and Optical Character Recognition (OCR) technique on insurance cards.

13. A non-transitory computer program product having embodied thereon a computer program for integrating a widget in a third-party application, the computer program product storing instructions for:

at the third-party application:

receive a widget software code related to insurance payment capture and verification, wherein the widget software code is one of a script or a web URL, and wherein the widget software code is plug and play;

integrate the widget software code into an application code of the third-party application; and execute the widget software code to invoke an insurance payment widget, wherein the insurance payment widget is configured to:

capture one or more insurance card images, wherein the one or more insurance card images are received from a user;

extract insurance information by an analysis of the insurance card images, wherein the insurance information is associated with an insurance provider, an insurance subscriber/Member ID (MID), and Group Number;

validate the extracted insurance information using a proprietary database of the insurance provider and insurance plans curated by an application provider;

automatically request, the insurance provider, for an insurance eligibility status and insurance coverage benefits of the insurance subscriber;

receive the insurance eligibility status and the insurance coverage benefits of the insurance subscriber from the insurance provider in real-time; and enable an insurance payment mode on the third-party application based on the received insurance eligibility status and the insurance coverage benefits in real-time, thereby integrating the widget in the third-party application.

\* \* \* \* \*